United States Patent [19]

Kotitschke et al.

[11] Patent Number: 5,075,425

[45] Date of Patent: Dec. 24, 1991

[54] PROCESS FOR THE PREPARATION OF A PHARMACEUTICAL WHICH CONTAINS IGG, IGA AND IGM AND CAN BE ADMINISTERED INTRAVENOUSLY

[75] Inventors: Ronald Kotitschke; Wolfgang Stephan, both of Dreieich; Wolfgang Möller, Oberursel; Detlef Piechaczek, Münster; Dieter Rudnick, Dreieich, all of Fed. Rep. of Germany

[73] Assignee: Biotest Pharma GmbH, Dreieich, Fed. Rep. of Germany

[21] Appl. No.: 561,033

[22] Filed: Aug. 1, 1990

[30] Foreign Application Priority Data

Aug. 17, 1989 [DE] Fed. Rep. of Germany ....... 3927112

[51] Int. Cl.$^5$ ............... C07K 3/28; C07K 15/14; A61K 39/395
[52] U.S. Cl. .................................. 530/387; 424/85.8
[58] Field of Search ..................... 530/387; 424/85.8

[56] References Cited

U.S. PATENT DOCUMENTS 4,318,902  3/1982  Stephan .......................... 530/387

FOREIGN PATENT DOCUMENTS 0013901  8/1980  European Pat. Off. ........... 530/387

*Primary Examiner*—Howard E. Schain
*Assistant Examiner*—Richard C. Ekstrom
*Attorney, Agent, or Firm*—Sprung Horn Kramer & Woods

[57] ABSTRACT

Process for the preparation of an immunoglobulin solution suitable for intravenous administration from a human blood protein fraction containing immunoglobulins IgG, IgA and IgM in partially concentrated from, with the process steps: addition of acetate buffer to the protein fraction, where appropriate removal of insoluble constituents by filtration, treatment with calcium phosphate and octanoic acid, centrifugation, removal of the supernatant and treatment thereof with an adsorbent, removal of the adsorbent and sterilization by filtration.

7 Claims, 2 Drawing Sheets

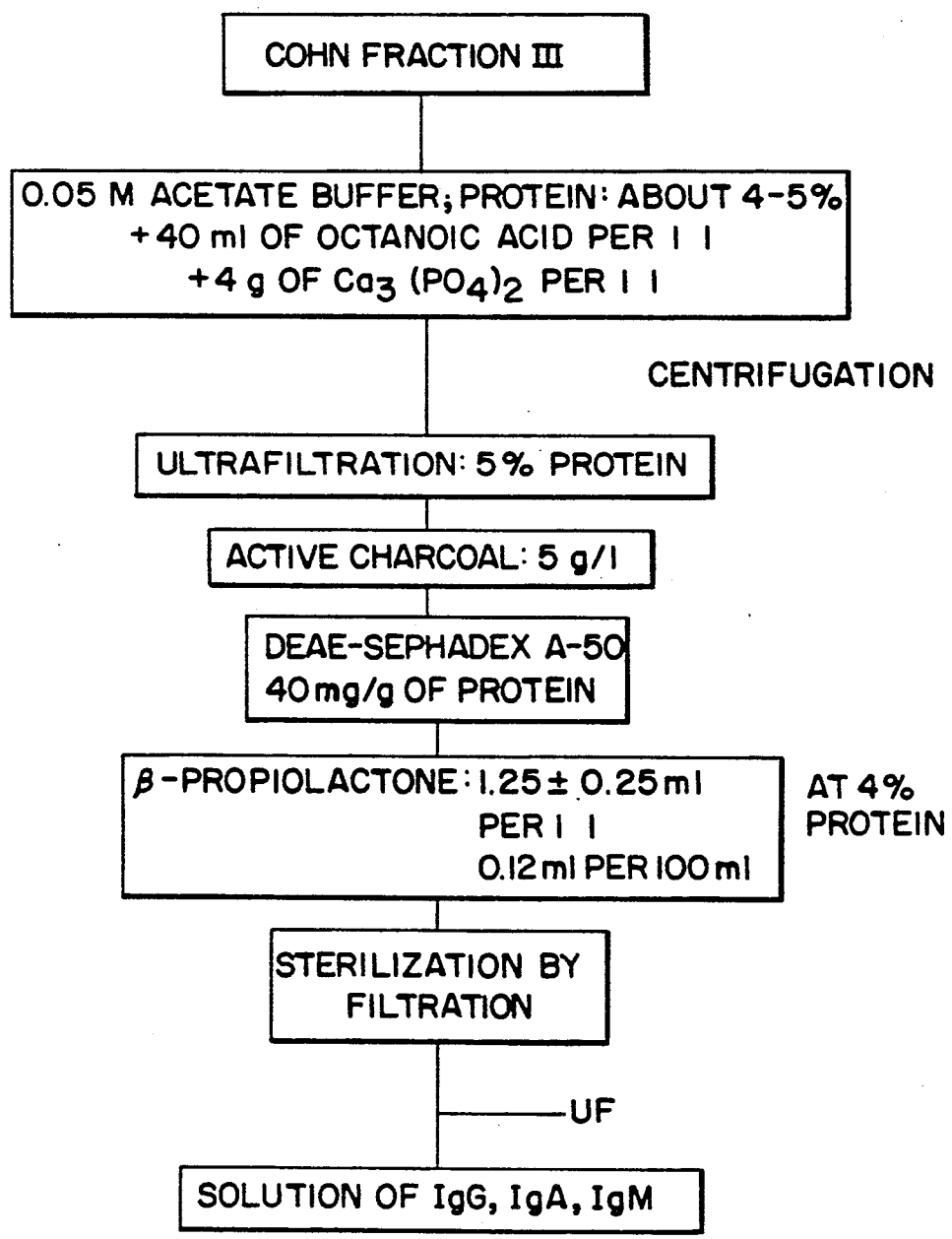

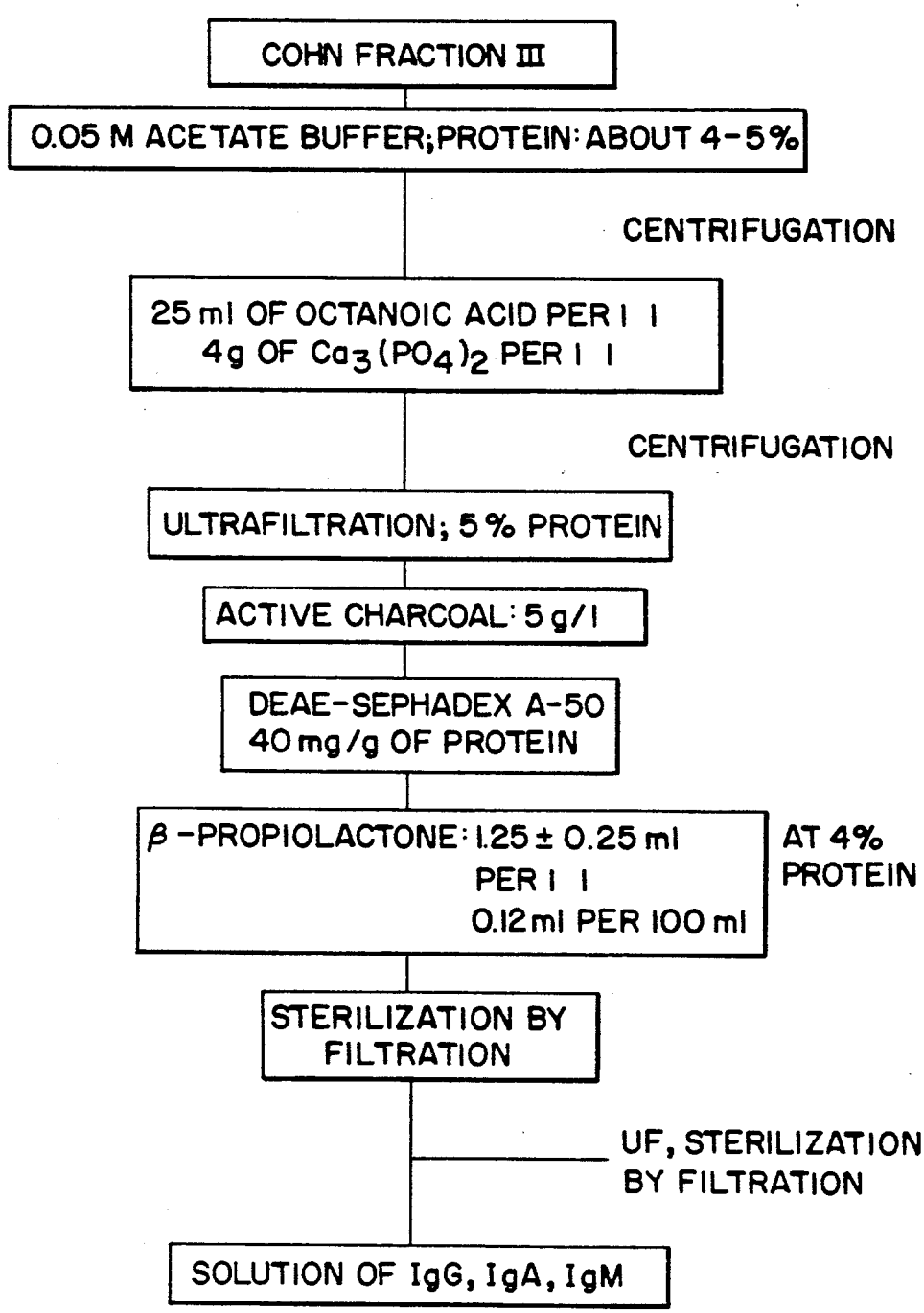

PROCESS FOR THE PREPARATION OF A PHARMACEUTICAL WHICH CONTAINS IGG, IGA AND IGM AND CAN BE ADMINISTERED INTRAVENOUSLY

The invention relates to a process for the preparation of an immunoglobulin solution suitable for intravenous administration, by treatment of a protein fraction which has been obtained by fractionation of human blood and which contains immunoglobulins of the IgG, IgA and IgM types in partially concentrated form.

EP 0 013 901 describes a process for the preparation of an IgM-containing protein solution which can be used intravenously, in which a protein fraction which has been obtained by fractionation from blood plasma or serum (such as, for example, a Cohn fraction III) is treated with colloidal silica to remove lipids, is treated with crosslinked dextrans or cellulose which carry diethylaminoethyl groups, preferably DEAE-Sephadex A 50, and is then treated with β-propiolactone at temperatures from 20 to 37° C. and pH values from 7.0 to 8.5 for a period of 2 to 10 hours until the pH is constant. Cohn fraction III contains considerable amounts of denatured protein, lipids and many proteases, besides the desired immunoglobulins. Responsible for the intravenous intolerance of Cohn fraction III are IgG polymers as well as the proteases with high proteolytic activities and other denatured proteins. The colloidal silica used in EP 0 013 901 is an agent suitable for removing lipids, but results in contact activation of coagulation factors and thus additionally increases the amounts of proteins with proteolytic activity contained in Cohn fraction III. It is therefore necessary in the process of EP 0 013 901 to use an anion exchanger of the DEAE-Sephadex A 50 type to adsorb these proteases. In the case of non-specific activation of proteases, reliable quantitative removal of these proteases is often possible only by using disproportionately large amounts of the appropriate adsorbent. It is also impossible to rule out, on contact activation of the proteins of the coagulation system and of the kinin system, release of proteolytic activities which do not bind to anion exchangers.

The present invention had the object of finding a process for the preparation of a sterile solution, which can be used intravenously, of immunoglobulins IgG, IgA and IgM by use of Cohn fraction III or of a protein fraction which has been obtained by fractionation from blood plasma or serum and which contains the immunoglobulins in enriched form.

It has now been found, surprisingly, that it is possible to dispense with the removal of lipids from Cohn fraction III by adsorption onto colloidal silica in order to prepare a solution of immunoglobulins IgG, IgA and IgM which can be used intravenously. FIG. 1 (annex) shows a diagram of the process according to the invention, and FIG. 2 (annex) depicts a variant.

Working up of Cohn fraction III by the method of EP 0 013 901 results in an intravenously tolerated solution which contains the immunoglobulins distributed in the following amounts: IgG: 4000 mg %; IgA: 500 mg % and IgM: 500 mg %, with a total protein content of 5 g %. Thus the ratio of IgG to IgM in this product is 8:1. The component in this product which is actively involved in treatment of bacterial infections is not only the IgM molecule but also the IgG contained in the product.

Human IgG consists of four subclasses (IgG-1, IgG-2, IgG-3 and IgG-4) with different chemical and biological properties. Initial contact with bacteria is followed by production first of antibodies of the IgM type which cause the bacteria to agglutinate and finally bring about complement-dependent lysis. The IgG antibodies which appear later normally have a higher affinity for the antigen, depending on the IgG subclass, induce an Fc-receptor-dependent phygocytosis or destruction via complement (F. Shakib, Derby: Basic and Clinical Aspects of IgG Subclasses); in Monographs in Allergy, Vol. 19 (1986), Karger).

The IgG subclass distribution after bacterial infections has been investigated in some studies, but mainly after vaccinations. The assignment of particular antibody activities to particular IgG subclasses is still a field of scientific research. However, as long as assignment is not possible, it is desirable to achieve in IgG-containing immunoglobulin products an IgG subclass distribution which corresponds maximally to that of a normal pooled plasma.

Table I shows that the use of colloidal silica during the preparation of IgG-containing immunoglobulin products results in a decrease in concentration, or even loss, of IgG subclass 3.

TABLE I

| | Influence of the amount of Aerosil on the IgG subclass distribution of polyvalent immunoglobulins | | | | | | | |
|---|---|---|---|---|---|---|---|---|
| Product | pH | Protein g/l | IgG g/l | Total lipids mg/dl | IgG-1 | 2 | 3 | 4 |
| | | | | | % distribution | | | |
| RGB-810 | 7.05 | 35.6 | 31.36 | 158 | 69.1 | 21.2 | 5.4 | 4.3 |
| RGB-810 + 0.5 AE | 6.89 | 34.7 | 30.15 | 28 | 70.8 | 22.1 | 2.7 | 4.4 |
| RGB-810 + 1.0 AE | 6.78 | 32.4 | 28.72 | 7 | 73.1 | 22.3 | 0.3 | 4.2 |

The immunoglobulin concentration was determined using the various methods which follows: The Mancini technique with Partigen ® plates from Behringwerke and Quantiplate ® from Kallestad and the Auto ICS II nephelometer from Beckmann. The reference material for IgC, IgA and IgM was the WHO standard 67/86 which contained 100 IU/ml. The IgG subclasses were determined by radial immunodiffusion on agarose plates using polyclonal subclass antisera (sheep) (from Janssen). The reference serum used was the WHO reference serum pool for immunoglobulin determination, because no official WHO standard for IgG subclass determination is available as yet. The total lipids were determined using reagents from E. Merck. The protein solution was heated with concentrated sulphuric acid and subsequently reacted with phosphoric acid/vanillin reagent.

The use of colloidal silica in a concentration of 3% Aerosil as described in EP 0 013 901 results in a decrease in the concentration of undesired lipids, but also causes loss of IgG subclass 3.

The property of colloidal silica of preferentially adsorbing IgG subclass 3 from protein solutions not only applies to IgG solutions which have already been highly purified, as detailed in Table I, but also generally applies to IgG-containing protein solutions as shown in the following table:

TABLE II

Influence of the amount of Aerosol on the IgG subclass distribution in serum protein solutions

| Product | pH | Protein g/l | IgG g/l | Total lipids mg/dl | IgG-1 | 2 | 3 | 4 |
|---|---|---|---|---|---|---|---|---|
| | | | | | % distribution | | | |
| RPCS 642 | 7.47 | 52.5 | 6.98 | 351 | 66.9 | 23.0 | 3.1 | 7.0 |
| RPCS 642 + 0.5% AE | 7.65 | 52.3 | 7.51 | 51 | 65.7 | 22.7 | 3.5 | 8.1 |
| RPCS 642 + 1.0% AE | 7.64 | 50.9 | 7.51 | 47 | 69.2 | 20.8 | 3.0 | 7.0 |
| RPCS 642 + 2.0% AE | 7.54 | 48.1 | 6.95 | 41 | 70.7 | 21.8 | 0.4 | 7.1 |

The product according to the invention contains IgG subclass 3 in a concentration which corresponds to a normal serum pool, whereas IgG subclass 3 is absent from a product treated with 3% Aerosil ® (AE), as is shown in Tab. III which follows:

TABLE III

| | IgG subclass distribution in % | | | |
|---|---|---|---|---|
| | IgG-1 | IgG-2 | IgG-3 | IgG-4 |
| IgG without AE treatment | 58.8 | 28.1 | 3.7 | 9.4 |
| IgG with AE treatment | 61.2 | 29.5 | 0.1 | 9.2 |
| Normal serum IgG* | 70–60 | 25–27 | 2.4–4.6 | 1.6–7.5 |

*Geigy table (1979) 125

There is a high risk that blood plasma fractions are infectious. This risk particularly relates to the transmission of hepatitis B and non-A, non-B hepatitis and, recently, HIV (human immunodeficiency virus). Since it is not possible by diagnostic measures to prepare hepatitis-safe blood products from plasma pools, various processes for the sterilization of blood constituents have been developed. Pasteurization (60° C., 10 h) is used successfully for albumin and has also been described, owing to the use of stabilizers such as amino acids and mono- or oligosaccharides and sugar alcohols, in recent years for the sterilization of sensitive plasma proteins such as coagulation factors II, VIII and XIII (EP 0 018 561). The efficacy of pasteurization in the presence of these stabilizers has yet to be established and is currently being tested. Heating immunoglobulins at 63° C. for 10 minutes results in a drastic increase in their anticomplementary activity, so that pasteurization is unsuitable for the sterilization of immunoglobulins (R. van Furth, A. G. P. Braat, P. C. J. Leijh, A. Gardi: Opsonic and physicochemical characteristics of intravenous immunoglobulin preparations. Vox Sang. 53: 70–75 (1987)).

The need also to subject immunoglobulin products to a sterilization measure is evident from a number of recent publications in which the transmission of hepatitis B and non-A, non-B hepatitis by intravenous immunoglobulin products has been described: Bj kander, J., Cunningham-Rundles, C., Lundin, P., Söderström, R., Hanson, L. A. (1988): Intravenous immunoglobulin prophylaxis causing liver damage in 16 or 77 patients with hypogammaglobulinemia of IgG subclass deficiency. Am. J. Med. 84: 107–111.

John, J. T., Ninan, G. T., Rajagopalan, M. S., John, F. et al (1979): Epidemic hepatitis B caused by commercial human immunoglobulin. Lancet I:1074.

Lever, A. M. L., Webster, A. V. D., Brown, D., Thomas H. C. (1984): Non-A, non-B hepatitis occurring in gammaglobulinaemic patients after intravenous immunoglobulin. Lancet II:1062–1064.

Lockner, D., Bratt, G., Lindborg, A., Tornebohm, E. (1987): Acute unidentified hepatitis in a hypogammaglobulinaemic patient on intravenous gammaglobulin successfully treated with interferon. Acta. Med. Scand. 221:413–415.

Williams, P. E., Yap, P. L., Gillon, J., Crawford, R. J., Galea, G., Cuthbertson, B. (1988). Non-A, non-B hepatitis transmission by intravenous immunoglobulin. Lancet II:501.

The method of low-temperature sterilization described by LoGrippo consists of combined treatment of human plasma with β-propiolactone and UV radiation (LoGrippo, G. A. u. Hayashi, H.: Henry Ford Hosp. Med. J. 21 (1973), 181; Logrippo, G. A. and Hartmann, F. W.: Bibl. Haematol. 7 (1958), 225).

The data published by LoGrippo show that only the combination of β-propiolactone with UV radiation resulted in virus-safe plasmas (LoGrippo, G. A.: A ten year clinical study of plasma treatd with Betaprone and combined Betaprone plus ultraviolet irradiation. Pacific Medicine and Surgery 72 (1964) 298–302).

In EP 0 013 901, β-propiolactone is used for treating an IgM-containing protein solution for the preparation of an immunoglobulin solution which can be administered intravenously.

The process according to the invention results, even without β-propiolactone treatment, in an immunoglobulin solution which is enriched in IgM and whose anticomplementary activity is about 600 CH 50/g of protein. Additional treatment with β-propiolactone or tri-n-butyl phosphate means that virus transmission by this product can be ruled out. Thus, treatment of the immunoglobulin solution solely with β-propiolactone, without additional UV radiation, suffices reliably to rule out transmission of non-A, non-B hepatitis too, as has been shown in an experiment on chimpanzees.

Another important difference between the process of EP 0 013 901 and the process according to the invention relates to the adsorption with an anion exchanger. In EP 0 013 901 Cohn fraction III is treated with the anion exchanger even before the octanoic acid treatment, whereas the process according to the invention carries out this process step only after the immunoglobulin solution has been treated with octanoic acid and active charcoal, in order to ensure that proteolytic activities appearing during working up of Cohn fraction III are reliably removed.

The object of EP 0 013 901 was to prepare from a protein fraction containing IgG, IgA and IgM (Cohn fraction III) a solution of these proteins which can be administered intravenously. It was necessary for this to use β-propiolactone to reduce the anticomplementary activity in the starting material. It has now been shown, surprisingly, that the process according to the invention improves the anticomplementary activity of the starting fraction so markedly that it is also possible to use other substances suitable for the sterilization of blood products, such as, for example, tri-n-butyl phosphate and β-propiolactone. For example, β-propiolactone may be used in amounts of 0.05 to 0.15 ml per 100 ml of a 4% strength immunoglobulin solution; tri-n-butyl phosphate may be used in amounts of 0.10 to 1.0 ml per 100 ml of a 5% strength immunoglobulin solution.

The levels of anticomplementary activity (ACA) and the in vivo tolerability of the products prepared by the process according to the invention, and the comparison products, are compiled in Table IV:

TABLE IV

| Product | Anticomplementary activity (ACA) and in vivo tolerability in the rat | |
|---|---|---|
| | ACA CH 50/g of protein | % change in blood pressure (n = 6) |
| IgM conc. of Ex. 1 without β-PL | 800 | −30 |
| IgM conc. of Ex. 1 with β-PL | 250 | −15 |
| IgM conc. of Ex. 2 without β-PL | 600 | −20 |
| IgM conc. of Ex. 2 with β-PL | 180 | −15 |
| reference IgG product (commercially available i.v. IgG product) | 80 | −8 |
| IgM conc. of EP 0 013 901 (without β-PL) | >1500 | −50 |
| IgM conc. of EP 0 013 901 (with β-PL) | 300 | −20 |
| Cohn fraction III or i.m. product | >1500 | −60 |

To determine the anticomplementary activity of the immunoglobulins, a defined amount of the test product was incubated with a defined amount of guinea-pig complement, and the remaining amount of complement was titrated. The ACA has been reported as consumption of CH-50 per g of immunoglobulin. The method for determining ACA substantially correspond to the method published by M. Mayer (Mayer, M. M. (1961). Complement and complement fixation. In: Experimental Immunochemistry, 2edn., pp 133–240, C. Thomas, Springfield, I).

An acceptable value for IgG products which can be used intravenously is regarded as being an anticomplementary activity (ACA) of ≦1500 CH 50 per g of protein. Cohn fraction III has ACA values > 1500 CH 50/g of protein and experience has shown that it is not tolerated intravenously.

The IgM-containing product of EP 0 013 901 has an ACA of 300 CH 50/g, and experience has shown that it is well tolerated on intravenous use. An in vivo model for testing the i.v. tolerability is the rat model of Bleeker et al. (W. K. Bleeker, J. Agterberg, G. Righter, A. de Vriesvan Rossen, J. C. Bakker: An animal model for the detection of hypotensive side effects of immunoglobulin preparations. Vox Sang. 52: 281–290 (1987).

The parameter of the immunoglobulin tolerability in this model is the blood pressure. Products which are not tolerated intravenously result in a distinct fall in blood pressure. Comparison of products which are not tolerated intravenously, that is to say products which can be used i.m. (intramuscularly), with the product of EP 0 013 901 and with the product according to the invention of Example 1 and 2 shows that the products prepared according to the invention result in a fall in rat blood pressure (see Table IV), which is distinctly less than that of i.m. products.

The examples which follow illustrate the invention:

EXAMPLE 1

3 kg of distilled water were added to each kg of Cohn fraction III paste. The product was cooled to a temperature of 4° C. 0.0055 kg of sodium acetate trihydrate were added for each 1 kg of distilled $H_2O$. The pH was adjusted to 5.05 by addition of 96% strength acetic acid. 50 kg of paste were suspended in 120 l of buffer solution at +4° C. The pH of the suspension was adjusted to 5.05 with 96% strength acetic acid. The precipitate was removed by centrifugation with a Cepa centrifuge. The solution which had been separated from the precipitate was warmed to +25° C. 25ml of octanoic acid were added for each kg of supernatant. The octanoic acid was added through a dropping funnel. The pH of the solution was adjusted to 4.8, and the mixture was left at +20° C. for 1 hour. 4 g of tricalcium phosphate were added for each kg of the mixture, and the mixture was left at 20° C. for 45 minutes before the suspension was centrifuged to remove the precipitate. The supernatant was filtered after the centrifugation and subsequently subjected to ultrafiltration. The solution which had undergone ultrafiltration against acetate buffer was adjusted to a protein level of 5% and a pH of 6.7. 5 g of active charcoal were added for each kg of this solution, while stirring slowly at room temperature. The adsorption time was 1 hour. The active charcoal was subsequently removed by centrifugation, and the supernatant as filtered. DEAE Sephadex A-50 which had been swollen in 0.08 M sodium acetate solution was added in an amount of 40 mg per g of protein to the filtered solution. The Sephadex adsorption took place at pH 6.5. After the Sephadex had been removed, the protein content of the eluate was adjusted to 40 g/l, and 1.40 ml of β-propiolactone were added for each 1 l of supernatant with the pH constant at 8.0–8.1. The pH was maintained constant by adding 1 N NaOH. The solution was sterilized by filtration after the β-propiolactone treatment. The solution which had been sterilized by filtration was subjected to ultra- and diafiltration to adjust the ion concentration and the protein level. This solution was sterilized by filtration and dispensed into 1-liter sterilized empty bottles.

EXAMPLE 2

The starting material was, as described in Example 1, Cohn fraction III which was suspended in 120 l of buffer solution per 50 kg of paste at +4° C. The pH was adjusted to 5.05 with 96% strength acetic acid. 40 ml of octanoic acid were added for each kg of the suspension via a dropping funnel at room temperature. The mixture was subsequently stirred for 15 minutes, and the pH was adjusted to 5.05 with 1 N NaOH. Subsequently 4 g of tricalcium phosphate were added for each kg of the mixture, and the mixture was left to stir at room temperature for 1 hour. It was subsequently centrifuged. The supernatant was subjected, as detailed in Example 1, to ultrafiltration and treatment with active charcoal, DEAE-Sephadex A-50 and β-propiolactone, before the solution was subjected to ultrafiltration, sterilized by filtration and bottled.

EXAMPLE 3

The starting material was, as described in Example 1, Cohn fraction III which was suspended in 120 l of buffer solution per 50 kg of paste at +4° C. The octanoic acid treatment and calcium phosphate adsorption were carried out as described in Example 1. The supernatant which had been filtered after centrifugation was mixed with the polyoxyethylene derivative Tween ® 80 in a concentration of 1% and, 15 minutes later, tri-n-butyl phosphate was added to a concentration of 0.3%. The mixture was stirred at +25° C. for 8 hours. Subsequently, 5% soy bean oil was added and, after stirring for 30 minutes, the aqueous phase was decanted from the oily phase, and the aqueous solution was subjected to ultrafiltration against acetate buffer. The protein level was adjusted to 5%, and the pH to 6.7. 5 g of active charcoal were added for each kg of this solution while stirring slowly at room temperature. The adsorption time was 1 hour. The active charcoal was subsequently removed by centrifugation, and the supernatant was filtered. DEAE-Sephadex A-50 which had been swollen in 0.08 M sodium acetate solution was added in an amount of 40 mg per g of protein to the filtered solution. The Sephadex adsorption took place at pH 6.5. After the Sephadex had been removed, the solution was subjected to ultra- and diafiltration to adjust the ion concentration and the protein level. This solution was sterilized by filtration and dispensed into 1-liter sterilized empty bottles.

It will be understood that the specification and examples are illustrative but not limitative of the present invention and that other embodiments within the spirit and scope of the invention will suggest themselves to those skilled in the art.

What is claimed is:

1. A process for the preparation of an immunoglobulin solution suitable for intravenous administration, from a protein fraction which has been obtained by fractionation of human blood and which contains the immunoglobulins of the IgG, IgA and IgM types in partially concentrated form, comprising
   a) adding acetate buffer to the protein fraction,
   b) adding calcium phosphate and octanoic acid to the protein fraction,
   c) centrifuging,
   d) subjecting the centrifuge supernatant solution to DEAE-Sephadex A 50 adsorption,
   e) removing the adsorber from the solution, and
   f) filtering the solution,
said process being conducted in the absence of colloidal silica.

2. A process according to claim 1, wherein between steps (a) and (b) any constituents insoluble in the acetate buffer are removed by centrifugation.

3. A process according to claim 1, wherein the supernatant is treated wtih active charcoal before the adsorption in step (d).

4. A process according to claim 1, including the step of treating the immunoglobulin solution with $\beta$-propiolactone.

5. A process according to claim 4, wherein about 0.05 to 0.15 ml of $\beta$-propiolactone is used per 100 ml of a 4 % strength immunoglobulin solution.

6. A process according to claim 1, wherein the immunoglobulin solution is treated with tri-n-butyl phosphate.

7. A process according to claim 6, wherein about 0.10 to 1.0 ml of tri-n-butyl phosphate is used per 100 ml of a 5% strength immunoglobulin solution.

* * * * *